(12) United States Patent
Chen et al.

(10) Patent No.: US 11,656,275 B2
(45) Date of Patent: May 23, 2023

(54) INJECTION DEVICE, SEMICONDUCTOR TESTING SYSTEM AND ITS TESTING METHOD

(71) Applicant: HERMES TESTING SOLUTIONS INC., Hsinchu (TW)

(72) Inventors: Bo-Lung Chen, Hsinchu (TW); Wen-Yuan Hsu, Hsinchu (TW)

(73) Assignee: HERMES TESTING SOLUTIONS INC., Hsinchu (TW)

(*) Notice: Subject to any disclaimer, the term of this patent is extended or adjusted under 35 U.S.C. 154(b) by 0 days.

(21) Appl. No.: 17/863,681

(22) Filed: Jul. 13, 2022

(65) Prior Publication Data

US 2022/0349939 A1 Nov. 3, 2022

Related U.S. Application Data

(62) Division of application No. 16/597,117, filed on Oct. 9, 2019.

(30) Foreign Application Priority Data

Jul. 5, 2019 (TW) .................................. 108123824

(51) Int. Cl.
*G01R 31/317* (2006.01)
*G01N 33/487* (2006.01)
(Continued)

(52) U.S. Cl.
CPC . *G01R 31/31702* (2013.01); *G01N 33/48707* (2013.01); *H01L 21/67* (2013.01);
(Continued)

(58) Field of Classification Search
CPC ....... G01R 31/31702; G01N 33/48707; G01N 33/48778; H01L 21/67; H01L 21/67017;
(Continued)

(56) References Cited

U.S. PATENT DOCUMENTS 5,787,885 A * 8/1998 Lemelson .............. A61B 5/083
600/573
6,062,224 A 5/2000 Kissinger et al.
(Continued)

FOREIGN PATENT DOCUMENTS

| CN | 103803479 A | 5/2014 |
| CN | 109647559 A | 4/2019 |

(Continued)

*Primary Examiner* — Jack Chiang
*Assistant Examiner* — Brandon Bowers
(74) *Attorney, Agent, or Firm* — Muncy, Geissler, Olds & Lowe, P.C.

(57) ABSTRACT

An injection device is disclosed herein. The injection device is utilized to inject a liquid onto a test area of a semiconductor element. The injection device includes a base, a reservoir, a first testing pipe, a cleaning pipe and a liquid-draining pipe. The reservoir set on the base is provided with at least one connecting port and a dropping port, wherein the dropping port is against the test area of the semiconductor element. The first testing pipe, the cleaning pipe and the liquid-draining pipe are connected to at least one connecting port, wherein a first liquid is injected from the first testing pipe into the reservoir, and wherein the a cleaning liquid is injected from the cleaning pipe into the reservoir to clean the reservoir and the test area. The dropping port is utilized to drain off the first testing liquid and the cleaning liquid in the reservoir. A semiconductor testing system utilizing the injection device and its testing method are also provided herein.

5 Claims, 11 Drawing Sheets

(51) Int. Cl.
*H01L 21/67* (2006.01)
*H01L 21/66* (2006.01)

(52) U.S. Cl.
CPC .... *H01L 21/6715* (2013.01); *H01L 21/67017* (2013.01); *H01L 22/20* (2013.01)

(58) Field of Classification Search
CPC .......................... H01L 21/6715; H01L 22/20; H01L 21/67051
See application file for complete search history.

(56) References Cited

U.S. PATENT DOCUMENTS

| | | | |
|---|---|---|---|
| 7,034,854 B2 * | 4/2006 | Cruchon-Dupeyrat | ...................... B82Y 10/00 346/140.1 |
| 9,625,493 B2 | 4/2017 | Liu et al. | |
| 2014/0134748 A1 | 5/2014 | Liu et al. | |
| 2018/0313777 A1 | 11/2018 | Wen et al. | |
| 2019/0001333 A1 | 1/2019 | Wen et al. | |

FOREIGN PATENT DOCUMENTS

| TW | 201833023 A | 9/2018 |
|---|---|---|
| TW | 201905432 A | 2/2019 |

* cited by examiner

INJECTION DEVICE, SEMICONDUCTOR TESTING SYSTEM AND ITS TESTING METHOD

CROSS REFERENCE TO RELATED APPLICATIONS

This application is a Divisional of co-pending application Ser. No. 16/597,117, filed on Oct. 9, 2019, for which priority is claimed under 35 U.S.C. § 120; and this application claims priority of Application No. 108123824 filed in Taiwan on Jul. 5, 2019 under 35 U.S.C. § 119, the entire contents of all of which are hereby incorporated by reference.

BACKGROUND OF THE INVENTION

1. Field of the Invention

The present invention relates to an injection device, a semiconductor testing system and a testing method thereof, particularly to an injection device, a semiconductor testing system and a testing method thereof, which inject a liquid onto a semiconductor chip to implement a test.

2. Description of the Prior Art

A biochip is a chip carrying a biosensor, which is a transducer using an immobilized biomolecule to detect an in-vivo or in-vitro chemical material or the interaction thereof. Further, a biosensor is a device for detecting a biomaterial substance based on the principles of electronics, electrochemistry, optics, and/or mechanics.

A biochip can be fabricated with a semiconductor process and can fast convert electric signals so that the biochips have been extensively used in integrated circuit field. In general, a semiconductor wafer contains tens to hundreds of IC chips. Before electric measurement, a wafer is normally diced into chips lest testing solutions cause short-circuit and damage surrounding IC chips. The testing solution is dripped onto the test area of the chip manually, and probes are used to measure the electric signals thereof. However, testing conditions are hard to control in the conventional testing method. The precision, quality and result of the manual testing method is likely to be suspected. Besides, the efficiency of the conventional testing method is poor.

Owing to the abovementioned conventional problems, the manufacturers are eager to develop an injection device and the testing method thereof, which can achieve precision measurement cost-efficiently.

SUMMARY OF THE INVENTION

The present invention provides an injection device, a semiconductor testing system and a testing method thereof, wherein a cleaning mechanism is built in the injection device to effectively reduce the risk that the testing liquid pollutes semiconductor elements, whereby to implement automatic and accurate tests.

In one embodiment, the present invention provides an injection device, which is used to inject a liquid onto a test area of a semiconductor element, and which comprises a base, a reservoir, a first testing pipe, a cleaning pipe, and a liquid-draining pipe. The reservoir is disposed on the base and includes at least one connecting port and a dropping port. The dropping port is slightly touching a test area of the semiconductor element. The first testing pipe, the cleaning pipe and the liquid-draining pipe are connected with the at least one connecting port. A first testing liquid is injected into the reservoir through first testing pipe. A cleaning liquid is injected into the reservoir through the cleaning pipe for cleaning the reservoir and the test area of the semiconductor element. The first testing liquid or the cleaning liquid is drained off from the reservoir through the liquid-draining pipe.

In one embodiment, the present invention provides a semiconductor testing system, which comprises a supporter, a testing member, an injection device, an actuating element and a test platform. The supporter supports a semiconductor element. The semiconductor element has a plurality of electrode pads and a test area. The testing member is disposed above the supporter. The testing member includes a plurality of electric-conduction elements and at least one opening, utilized to test the electric signals of the semiconductor element, wherein the position of the opening is corresponding to the test area. The injection device is utilized to inject a liquid onto a test area of the semiconductor element. The injection device includes a base, a reservoir, a first testing pipe, a cleaning pipe, and a liquid-draining pipe. The reservoir is disposed on the base and includes at least one connecting port and a dropping port. The dropping port is slightly touching a test area of the semiconductor element. The first testing pipe, the cleaning pipe and the liquid-draining pipe are connected with the at least one connecting port. A first testing liquid is injected into the reservoir through the first testing pipe. A cleaning liquid is injected into the reservoir through the cleaning pipe for cleaning the reservoir and the test area of the semiconductor element. The first testing liquid or the cleaning liquid is drained off from the reservoir through liquid-draining pipe. The actuating element is coupled to the injection device, actuating the injection device to make the dropping port of the injection device slightly touch or depart from the test area of the semiconductor element. The test platform is electrically connected with the testing member, the injection device and the actuating element to provide at least one of an electric power and a testing signal to the testing member, the injection device and the actuating element.

In one embodiment, the present invention proposes a semiconductor testing method, which comprises the following steps: placing a semiconductor element on a supporter, wherein the semiconductor element has a plurality of electrode pads and a test area; providing a testing member including a plurality of electric-conduction elements and at least one opening, wherein the position of the opening is corresponding to the test area, and wherein the plurality of electric-conduction elements contacts the electrode pads of the semiconductor element; providing an injection device including at least one connecting port and a dropping port; actuating the dropping port of the injection device to pass through the opening of the testing member and contact the test area of the semiconductor element; injecting a first testing liquid through the at least one connecting port of the injection device into a reservoir, and letting the first testing liquid contact the test area of the semiconductor element through the dropping port for testing electric signals of the semiconductor element; injecting a cleaning liquid through at least one connecting port of the injection device into the reservoir for cleaning the reservoir and the test area of the semiconductor element; and actuating the dropping port of the injection device to depart from the test area of the semiconductor element.

Below, embodiments are described in detail in cooperation with the attached drawings to make easily understood the objectives, technical contents, characteristics and accomplishments of the present invention.

DESCRIPTION OF THE PREFERRED EMBODIMENTS

The present invention will be described in detail with embodiments and attached drawings below. However, these embodiments are only to exemplify the present invention but not to limit the scope of the present invention. In addition to the embodiments described in the specification, the present invention also applies to other embodiments. Further, any modification, variation, or substitution, which can be easily made by the persons skilled in that art according to the embodiment of the present invention, is to be also included within the scope of the present invention, which is based on the claims stated below. Although many special details are provided herein to make the readers more fully understand the present invention, the present invention can still be practiced under a condition that these special details are partially or completely omitted. Besides, the elements or steps, which are well known by the persons skilled in the art, are not described herein lest the present invention be limited unnecessarily. Similar or identical elements are denoted with similar or identical symbols in the drawings. It should be noted: the drawings are only to depict the present invention schematically but not to show the real dimensions or quantities of the present invention. Besides, matterless details are not necessarily depicted in the drawings to achieve conciseness of the drawings.

Figure 1:
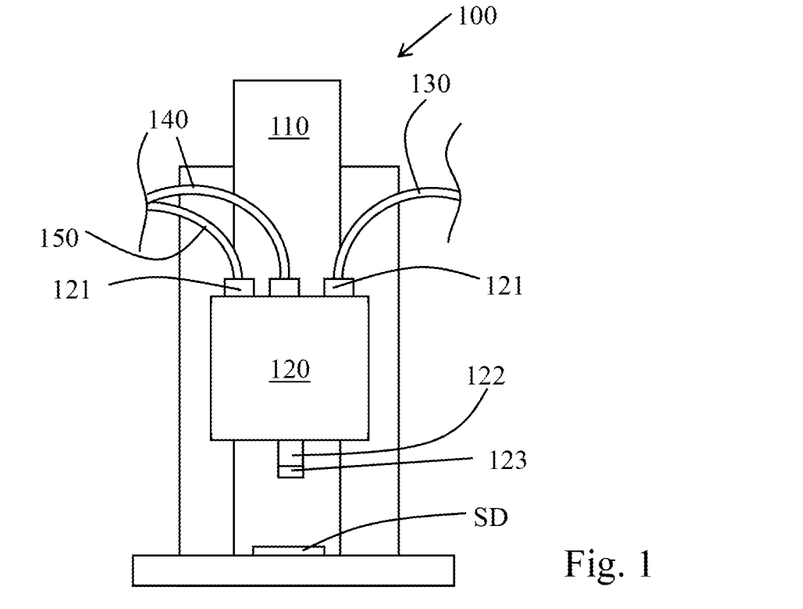
FIGS. 1-6 are diagrams respectively schematically showing injection devices according to different embodiments of the present invention.

Refer to FIG. 1. In one embodiment, the injection device 100 of the present invention is utilized to inject a liquid onto a test area of a semiconductor element SD to test the function of the semiconductor element SD. In one embodiment, the semiconductor element SD may be but is not limited to be a wafer, a single chip, or a semiconductor package. In another embodiment, the semiconductor element SD may be a wafer for fabricating biochips, a single biochip, or a packaged biochip. As shown in FIG. 1, the injection device 100 includes a base 110, a reservoir 120, a first testing pipe 130, a cleaning pipe 140 and a liquid-draining pipe 150. The reservoir 120 is disposed on the base 110 and the shape of the reservoir 120 is not limited by the shapes shown in the drawings. The reservoir 120 includes at least one connecting port 121 and a dropping port 122, wherein the dropping port 122 is slightly touching the test area of the semiconductor element SD. The first testing pipe 130, the cleaning pipe 140 and the liquid-draining pipe 150 are connected with the at least one connecting port 121 of the reservoir 120. A first testing liquid is injected into the reservoir 120 through first testing pipe 130. In another embodiment, a test adhesive can be used in the liquid-dropping tests. A cleaning liquid is injected into the reservoir 120 from the cleaning pipe 140 for cleaning the reservoir 120 and the test area of the semiconductor element SD. The first testing liquid or the cleaning liquid is drained off from the reservoir 120 via the liquid-draining pipe 150. The liquid inside the reservoir 120 may be drained out through the liquid-draining pipe 150 in a suction method or another appropriate method. In one embodiment, the injection device 110 includes a buffer element 123, which is disposed in the dropping port 122 of the injection device 120 and slightly touching the test area of the semiconductor element SD, whereby to buffer the impact stress generated by the dropping port 122 slightly touching the semiconductor element SD.

Figure 2:
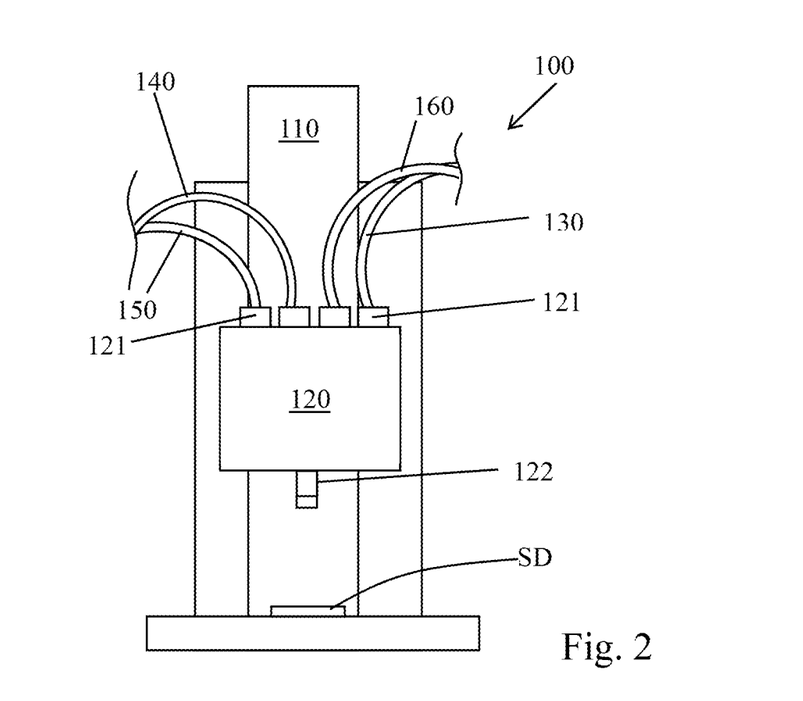
Figure 3:
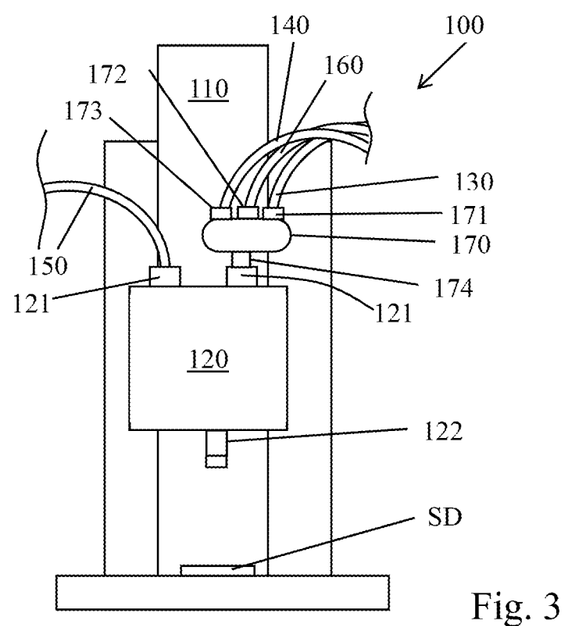
Figure 4:
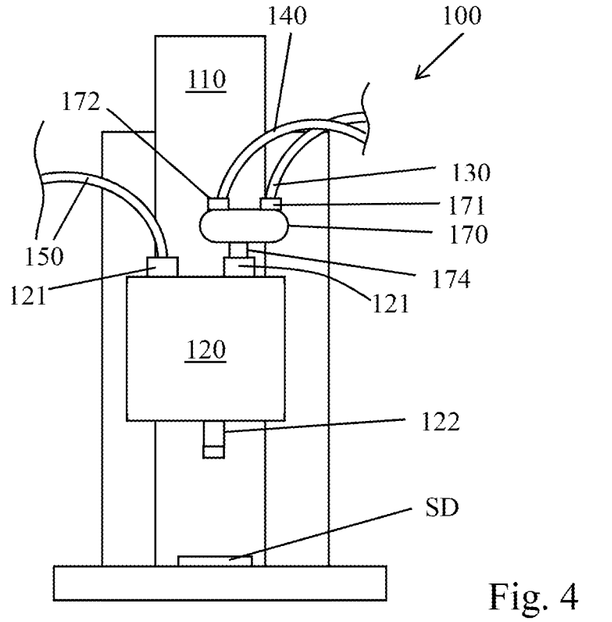
Figure 5:
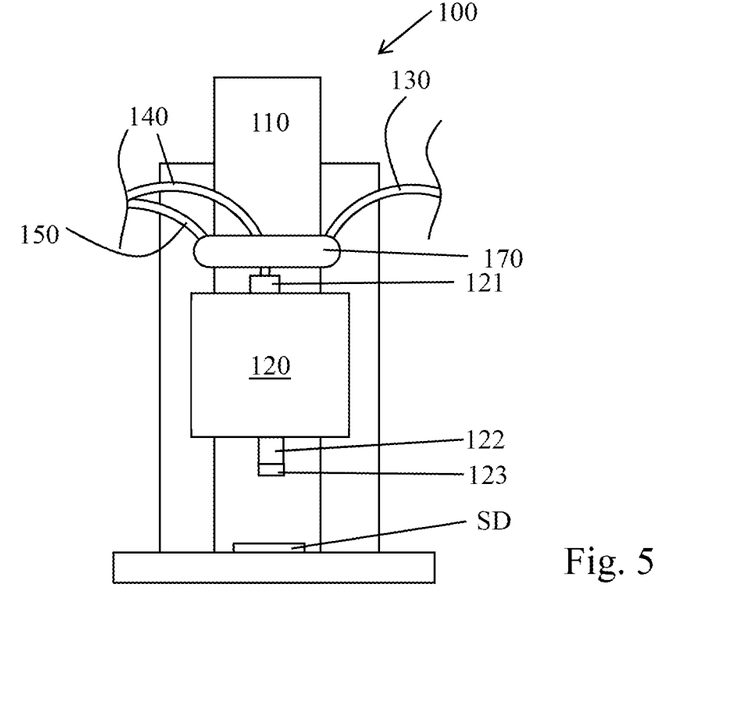

Refer to FIG. 2. In another embodiment, the injection device 100 further includes a second testing pipe 160. The second testing pipe 160 is connected with at least one connecting port 121 of the reservoir 120 and utilized to inject a second testing liquid into the reservoir 120. According to different designs of fabrication processes, the first testing liquid and the second testing liquid may be identical or different. In one embodiment, the injection device 100 includes a plurality of second testing pipes 160 respectively providing identical or different second testing liquid. Refer to FIGS. 3-5. In one embodiment, the injection device 100 further includes a multiport valve 170. The multiport valve 170 is disposed between the connecting port 121 and the abovementioned pipes. In the embodiment shown in FIG. 3, the multiport valve 170 includes at least three inlets 171, 172 and 173, and an outlet 174, wherein the first testing pipe 130, the second testing pipe 160 and the cleaning pipe 140 are respectively connected with the at least three inlets 171, 172 and 173, and wherein the outlet 174 is connected with the at least one connecting port 121 of the reservoir 120. In the embodiment shown in FIG. 4, the multiport valve 170 includes at least two inlets 171 and 172 and an outlet 174, wherein the first testing pipe 130 and the cleaning pipe 140 are respectively connected with the at least two inlets 171 and 172, and wherein the outlet 174 is connected with the at least one connecting port 121 of the reservoir 120. In the embodiment shown in FIG. 5, the multiport valve 170 includes at least three inlets 171, 172 and 173, and an outlet 174, wherein the first testing pipe 130, the cleaning pipe 140 and the liquid-draining pipe 150 are respectively connected with at least three inlets 171, 172 and 173, and wherein the outlet 174 is connected with the at least one connecting port 121 of the reservoir 120. In the abovementioned embodiments, the number of the inlets of the multiport valve 170 is corresponding to the number of the pipes. In one embodiment, the reservoir 120 includes a plurality of dropping ports 122 and are arranged in line or in an array, whereby the liquid-dropping tests of a plurality of semiconductor elements may be undertaken simultaneously (not shown in the drawings).

Figure 6:
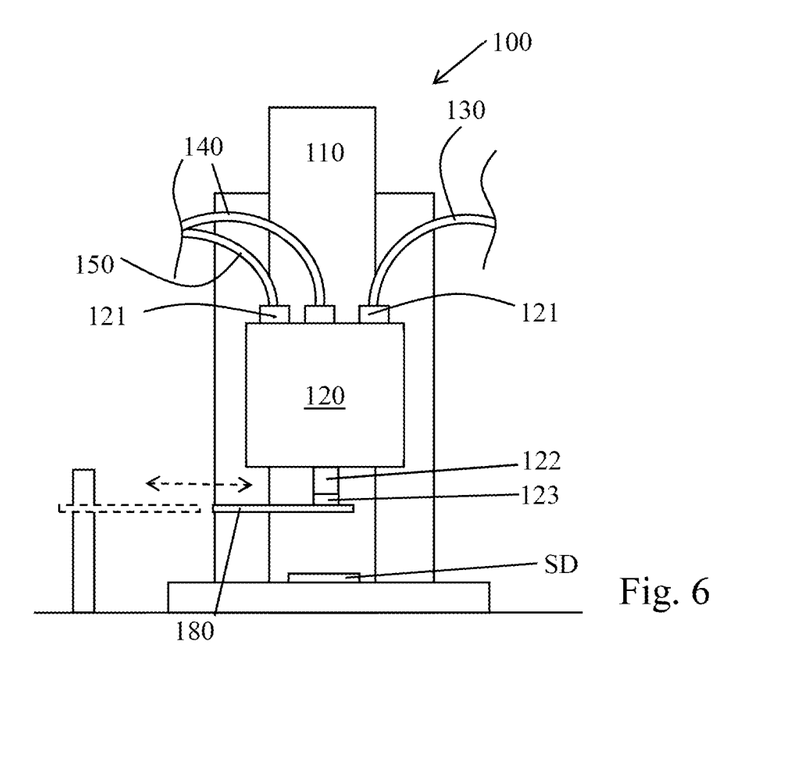

Refer to FIG. 6. In one embodiment, the injection device 100 further includes a blocking element 180. The blocking element 180 may be selectively pressed against the dropping port 122, whereby the reservoir 120 may be cleaned before test. Alternatively, after the semiconductor element SD has been cleaned, the blocking element 180 may be used to prevent the cleaning liquid from dropping and contaminating the semiconductor element SD. The blocking element 180 can be selectively utilized. During the cleaning step if the semiconductor element SD must be kept clean, the blocking element 180 is utilized to separate the cleaning liquid from the semiconductor element SD. On the other hand, it can be understood that the dropping port 122 (or buffer element 123) can directly contact the semiconductor element SD during the cleaning step if the pollution problem of the semiconductor element SD is a minor issue in some kind of testing procedure.

Figures 7A, 7B, 7C:
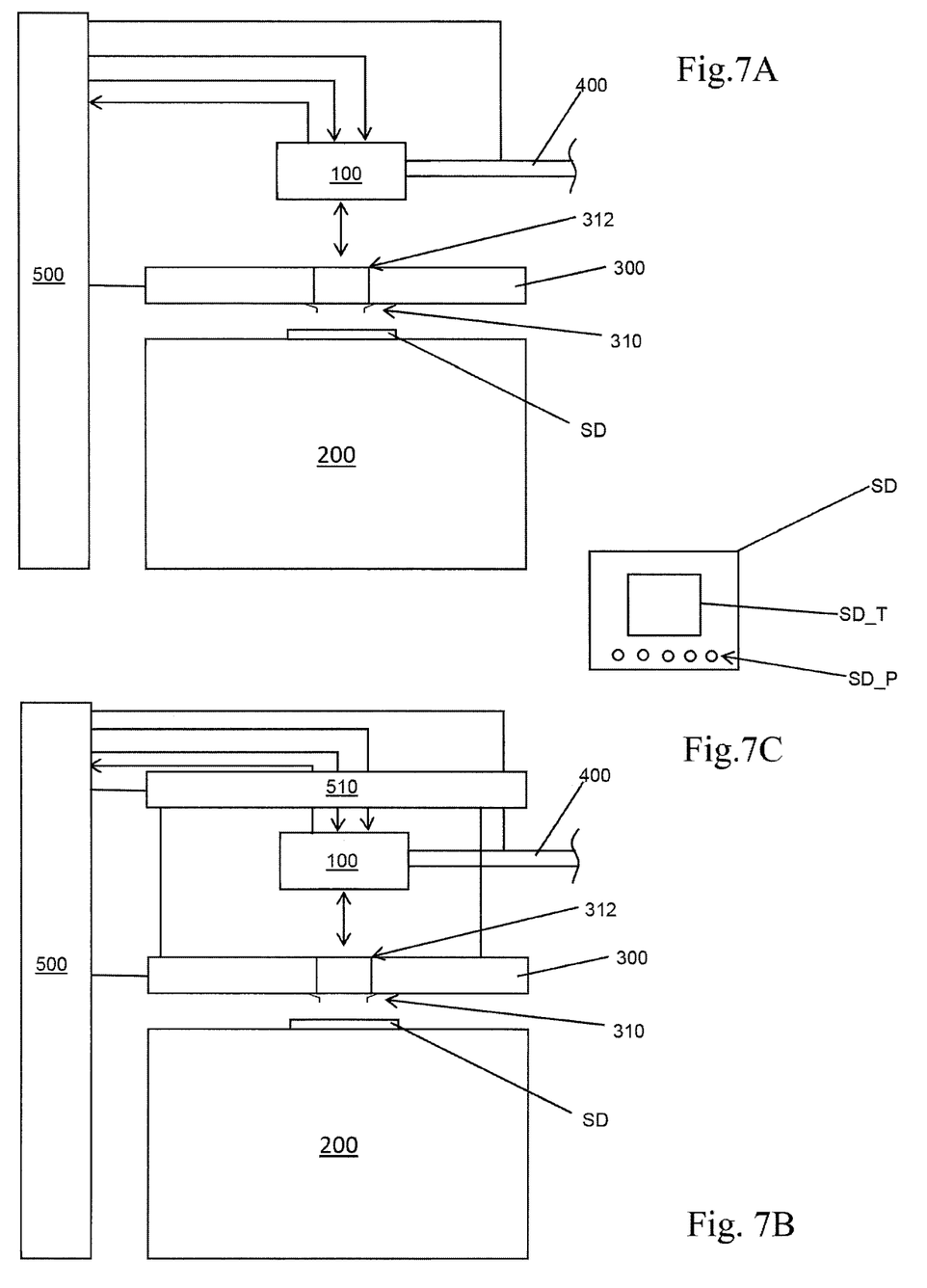
FIG. 7A and FIG. 7B are diagrams respectively schematically showing semiconductor testing systems according to different embodiments of the present invention.
FIG. 7C is a diagram schematically showing a semiconductor element according to one embodiment of the present invention.

Refer to FIGS. 7A, 7B and 7C. FIG. 7A and FIG. 7B respectively show the semiconductor testing systems according to different embodiments of the present invention. FIG. 7C shows a semiconductor element according to one embodiment of the present invention. In one embodiment, the semiconductor testing system of the present invention includes a supporter 200, a testing member 300, an injection device 100, an actuating element 400 and a test platform 500. The supporter 200 supports a semiconductor element SD, wherein the semiconductor element SD includes a plurality of electrode pads SD_P and a test area SD_T. It should be understood that the positions and configuration of the electrode pads SD_P and the test area SD_T are not limited by the drawings. The semiconductor element SD may be but is not limited to be a wafer, a single chip, or a semiconductor package. The testing member 300 is disposed above the supporter 200. The testing member 300 includes a plurality of electric-conduction elements 310 and at least one opening 312. The testing member 300 is utilized to test the electric signals of the semiconductor element SD. The position of the opening 312 is corresponding to the test area SD_T. The injection device 100 includes a base, a reservoir, a first testing pipe, a cleaning pipe, and a liquid-draining pipe. The detailed structure of the injection device 100 has been described in the abovementioned embodiments and will not be repeated herein. The actuating element 400 is coupled to the injection device 100, actuating the injection device 100 to make the dropping port 122 of the injection device 100 slightly touch or depart from the test area SD_T of the semiconductor element SD (refer to FIG. 1). For example, the actuating element 400 may drive the injection device 100 to descend or ascend to slightly touch or depart from the test area SD_T of the semiconductor element SD. The test platform 500 is electrically connected with the testing member 300, the injection device 100 and the actuating element 400, providing at least one of an electric power and a testing signal to the testing member 300, the injection device 100 and the actuating element 400. In one embodiment, the injection device 100 has a plurality of dropping ports 122 arranged in line or in an array, and a plurality of semiconductor elements is tested simultaneously (not shown in the drawings); in such a case, the testing member has a big opening or has a plurality of openings. While the testing member has a plurality of openings, the number of the opening matches or does not match the number of the dropping ports, and tests are undertaken in batches.

The semiconductor testing system of the present invention may be applied to different stages of tests, such as the chip probing (CP) stage and the final test (FT) stage. In one embodiment, the supporter 200 is a supporter of a semiconductor prober in the CP stage; the testing member 300 includes a probe card; the plurality of electric-conduction elements 310 are probes; and the probes are electrically connected with the electrode pads SD_P. Refer to FIG. 7B. In one embodiment, the test platform 500 includes a testing head 510, which is used to test the semiconductor elements SD. In one embodiment, the supporter 200 is a supporter of a test handler in the FT stage; the testing member 300 at least includes a test socket; the plurality of electric-conduction elements 310 is a plurality of electric-conduction contacts; the electric-conduction contacts are electrically connected with the electrode pads SD_P. The various embodiments of the injection device have been described above and will not be repeated herein. Thereby, the semiconductor testing system of the present invention can automatically inspect semiconductor elements and has an injection device able to clean itself and reduce the contamination of semiconductor elements.

Figure 8:
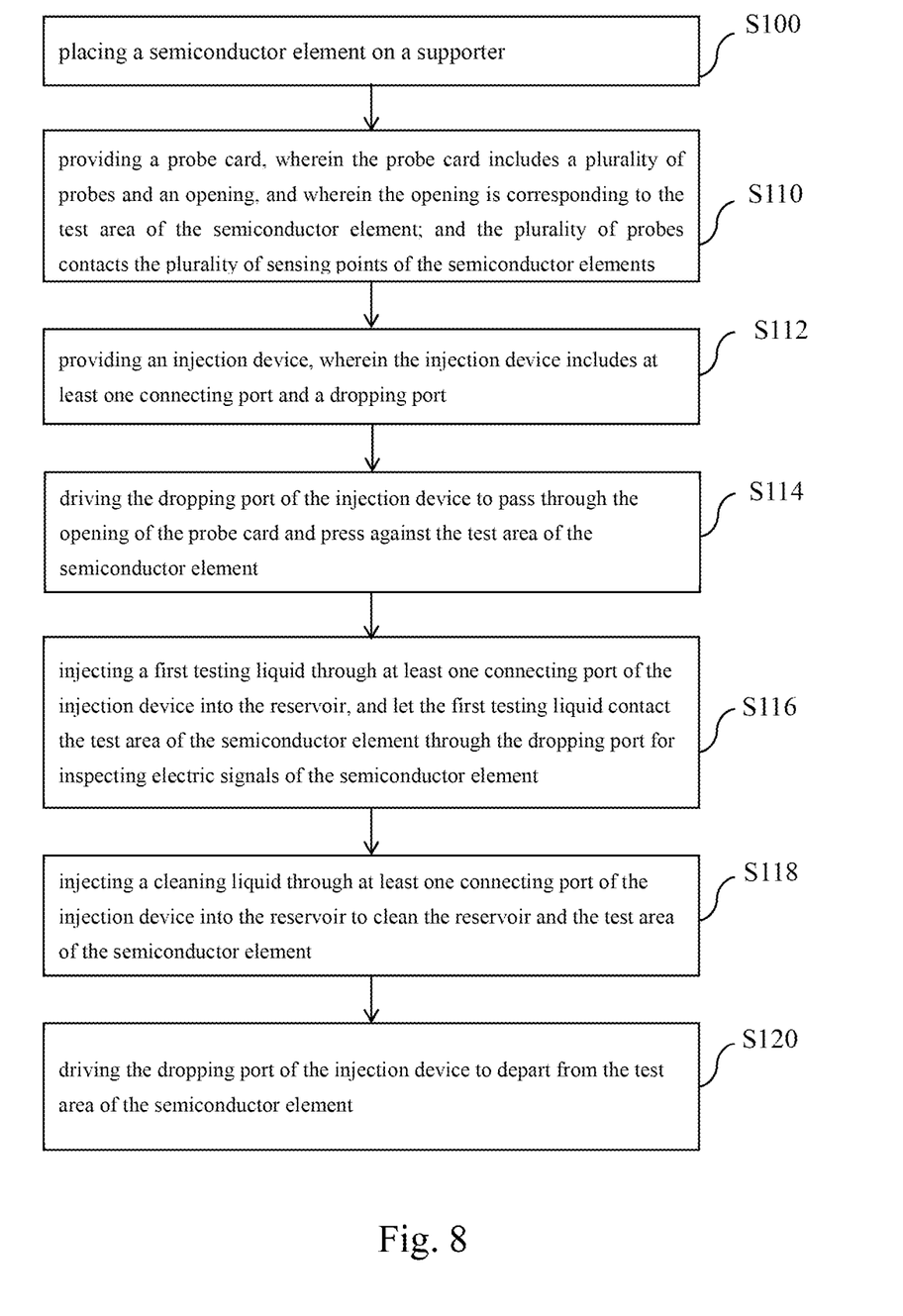
FIGS. 8-14 are flowcharts respectively showing semiconductor testing methods according to different embodiments of the present invention.

Refer to FIG. 8. In one embodiment, the semiconductor testing method of the present invention includes the following steps. Firstly, an appropriate method is utilized to place a semiconductor element on a supporter (Step S100), wherein the semiconductor element has a plurality of electrode pads and a test area, and wherein the positions and layout of the electrode pads and the test area are not limited by FIG. 7C. Next, provide a testing member, wherein the testing member includes a plurality of electric-conduction elements and at least one opening, and wherein the position of the opening is corresponding to the test area of the semiconductor element, and wherein the plurality of electric-conduction elements contacts the plurality of electrode pads of the semiconductor elements (Step S110). In one embodiment, the electric-conduction elements are disposed between the testing member and the semiconductor element. Next, an injection device is provided, wherein the injection device includes a reservoir, and wherein the reservoir has at least one connecting port and a dropping port (Step S112). In one embodiment, the dropping port faces the semiconductor element. Next, the dropping port of the injection device is driven to move and pass through the opening of the testing member and slightly touch the test area of the semiconductor element (Step S114). Next, a first testing liquid is injected through one connecting port of the injection device into the reservoir, and the first testing liquid contacts the test area of the semiconductor element through the dropping port to enable the test platform 500 to test the electric signals of the semiconductor element (Step S116). Next, a cleaning liquid is injected through one connecting port of the injection device into the reservoir to clean the reservoir and the test area of the semiconductor element (Step S118). Next, the dropping port of the injection device is driven to depart from the test area of the semiconductor element (Step S120). Thereby are completed the steps of testing electric properties, cleaning the reservoir, and cleaning the semiconductor element. The semiconductor testing method of the present invention may be applied to different stages of tests, such as the chip probing (CP) stage and the final test (FT) stage.

Figure 9:
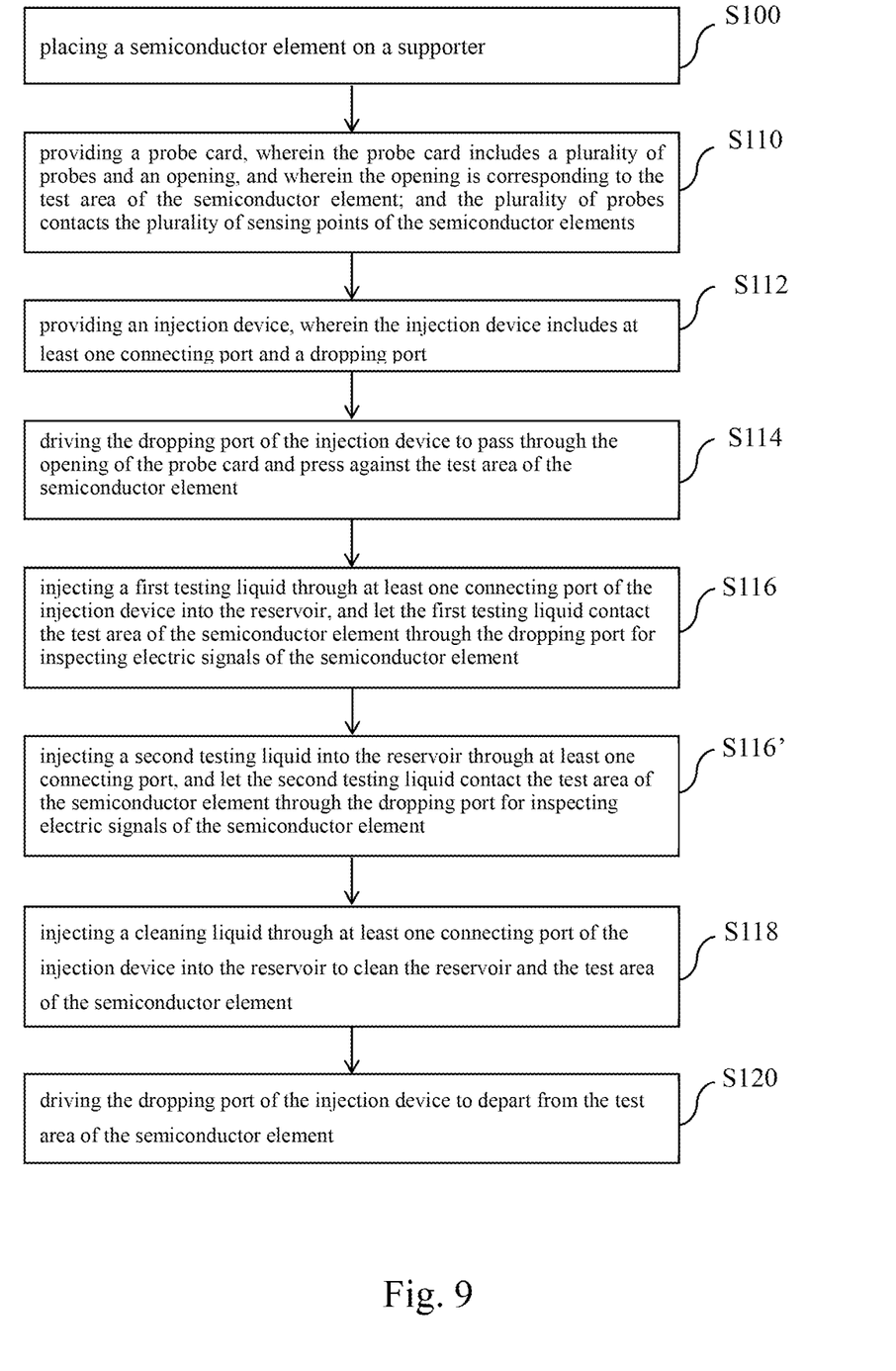
Figure 10:
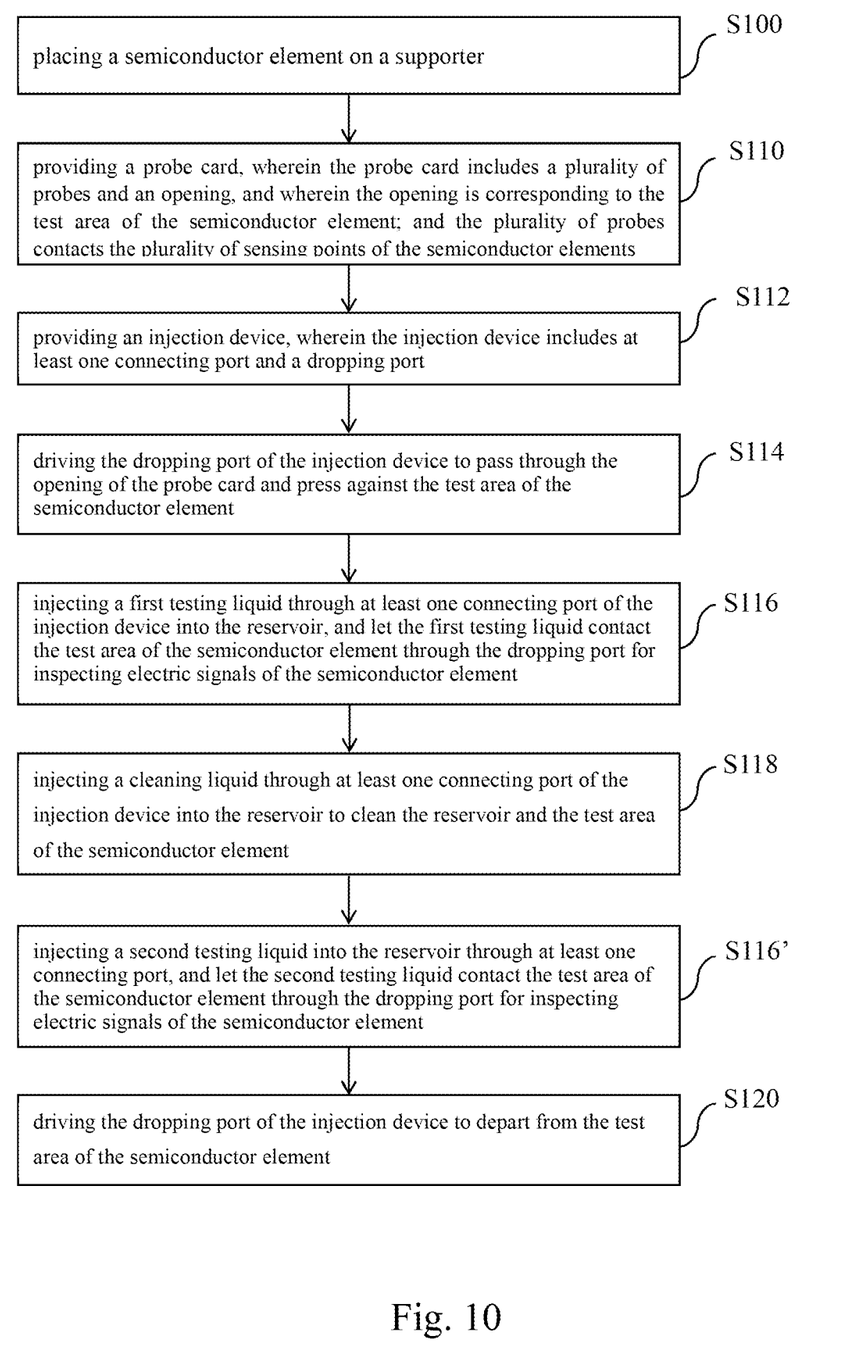
Figure 11:
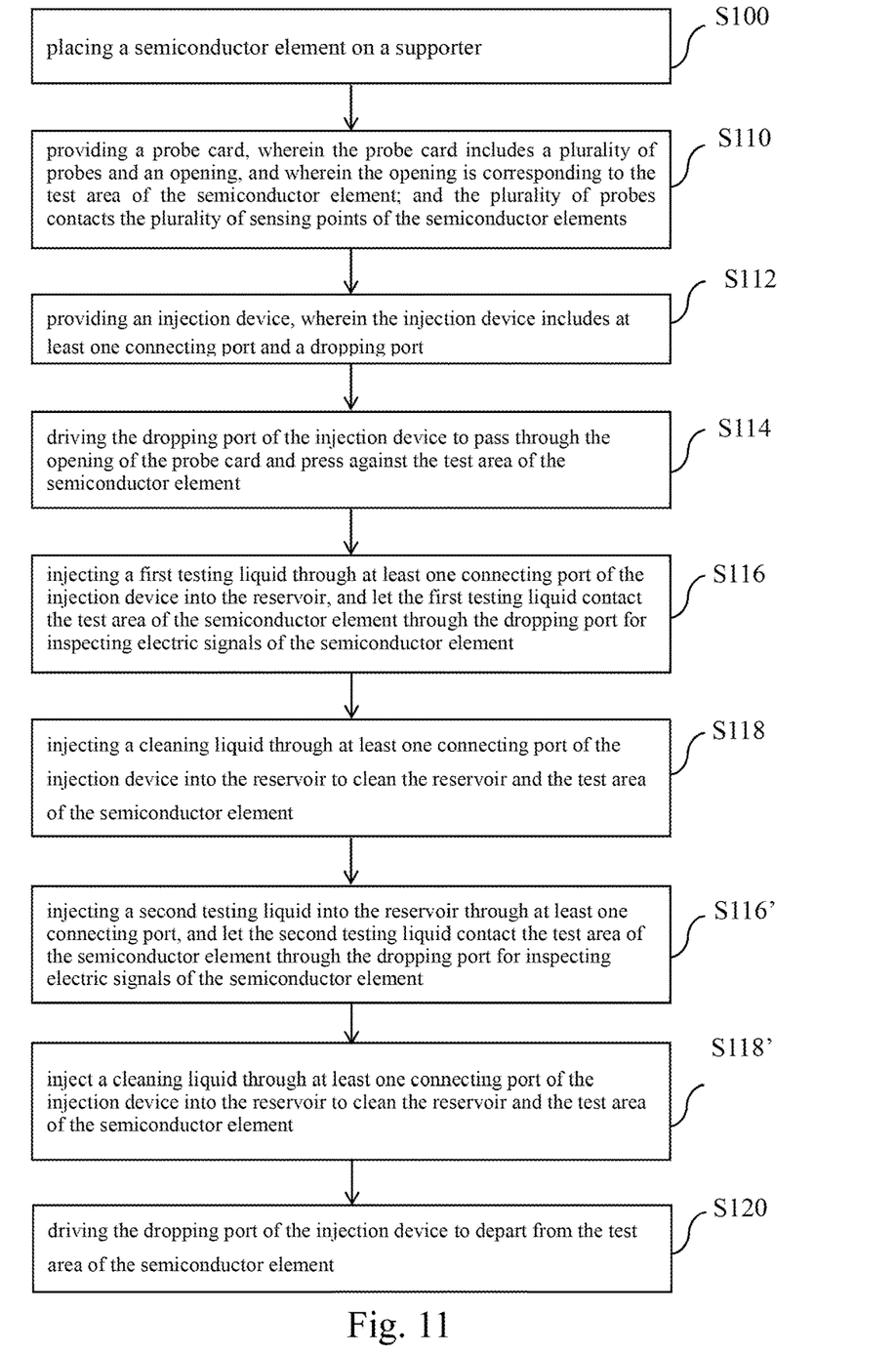

Refer to FIG. 9 and FIG. 10 for other embodiments of the semiconductor testing method of the present invention. In the case that several testing liquids must be used in test or the case that an identical testing liquid must be used repeatedly several times, the semiconductor testing method of the present invention further includes a step: before separating the dropping port of the injection device from the test area of the semiconductor element, such as before Step S118 (the cleaning step), a second testing liquid is injected from one connecting port of the injection device into the reservoir, and the second testing liquid drop down and contact the test area of the semiconductor element via the dropping port for testing the electric signals of the semiconductor element (Step S116'), as shown in FIG. 9. Alternatively, before separating the dropping port of the injection device from the test area of the semiconductor element, such as after Step S118 (the cleaning step) and before Step S120, a second testing liquid is injected from one connecting port of the injection device into the reservoir to let the second testing liquid drop down and contact the test area of the semiconductor element for testing the electric signals of the semiconductor element (Step S116'), as shown in FIG. 10. In another embodiment, after each cycle of dropping a testing liquid and testing the electric signals of the semiconductor element, a cleaning step, such as Step S118 or Step S118' in FIG. 11, is undertaken immediately.

Figure 12:
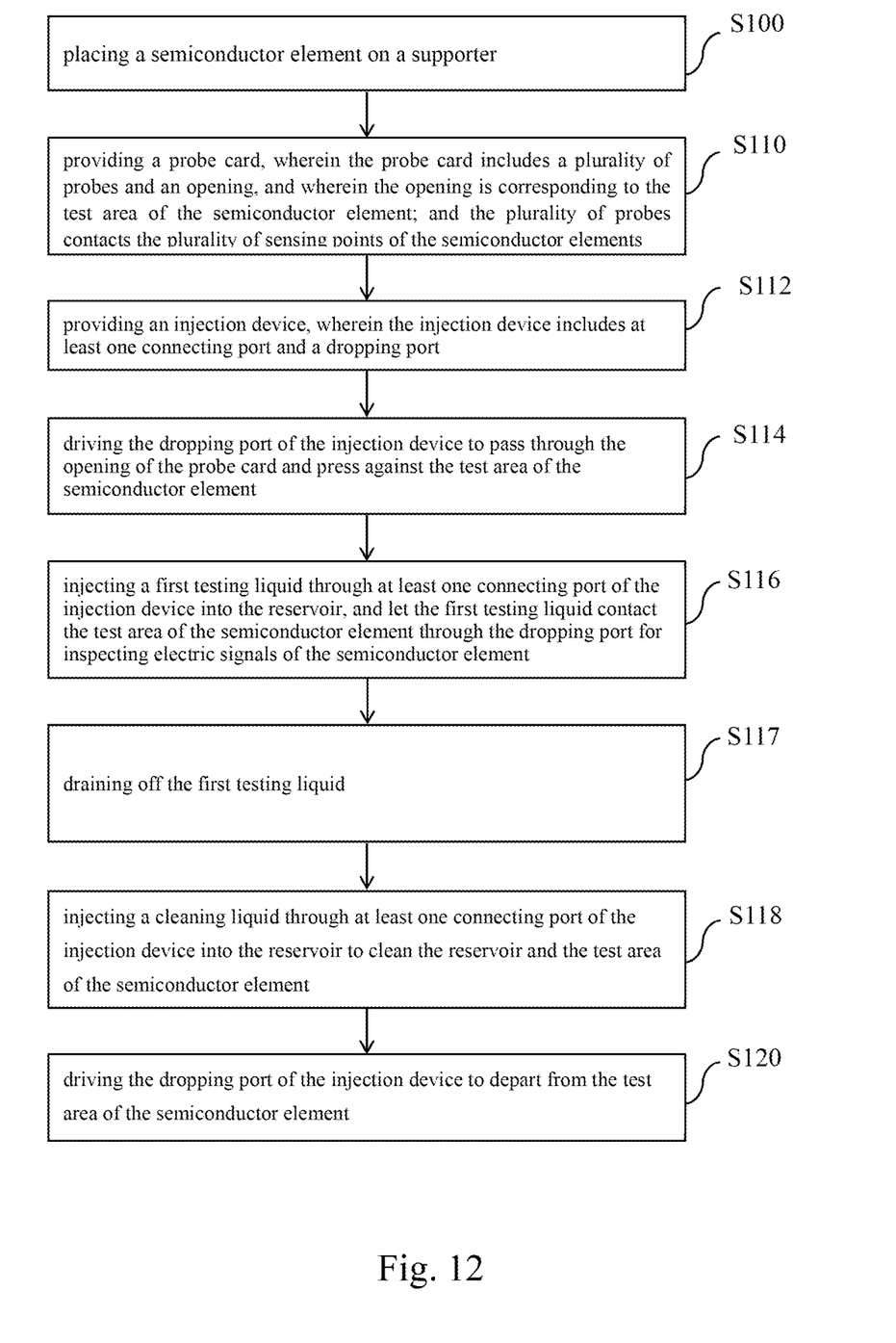
Figure 13:
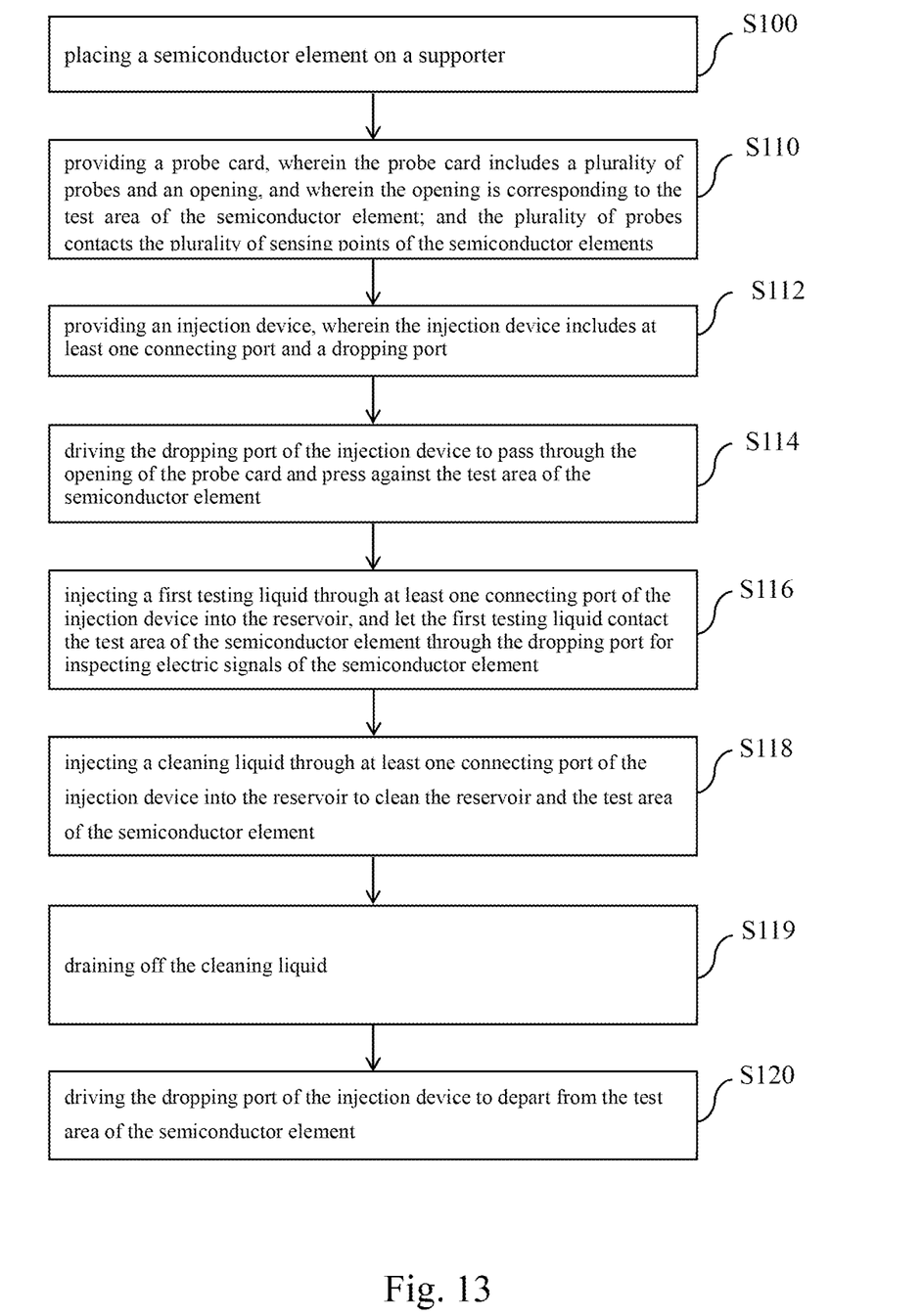

Refer to FIG. 12 for yet another embodiment of the present invention. In this embodiment, the semiconductor testing method of the present invention further includes a step: the first testing liquid is siphoned off (Step S117) before injecting the cleaning liquid, such as before Step S118 (the cleaning step), to reduce the risk that the residual testing liquid remains on the semiconductor element. In still another embodiment, the cleaning liquid is drained off (Step S119) before separating the dropping port of the injection device from the test area of the semiconductor element (such as before Step S120), as shown in FIG. 13.

Figure 14:
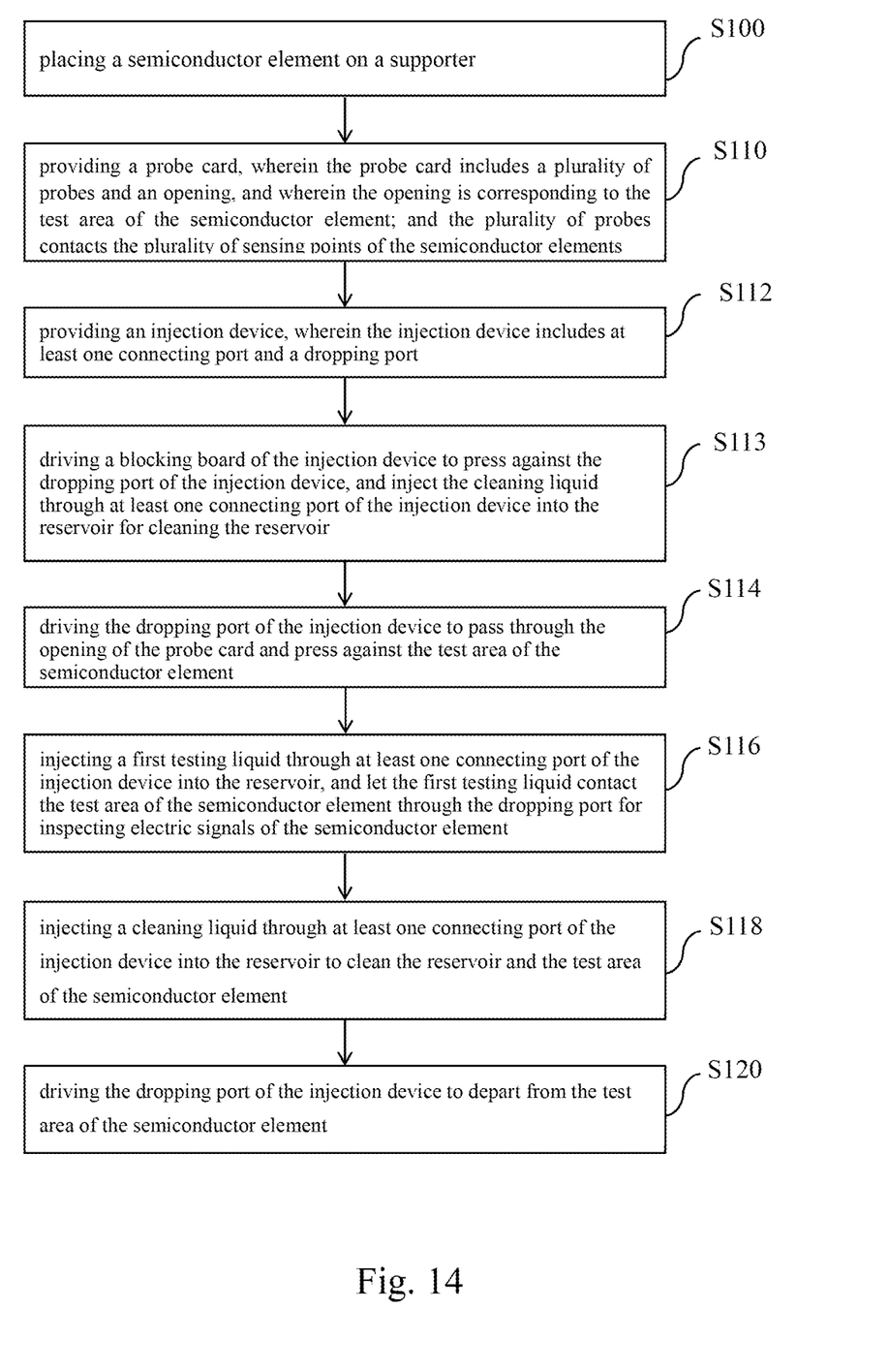

Refer to FIG. 14 for further another embodiment of the present invention. In this embodiment, a self-cleaning step is undertaken while the semiconductor testing system is used for the first time, or while the semiconductor testing system is utilized at the first time in each batch of tests, or in an appropriate timing. In other words, before the dropping port of the injection device is slightly touching the test area of the semiconductor element (such as before Step S114), a blocking element of the injection device is driven to press against the dropping port of the injection device, and the cleaning liquid is injected through the at least one connecting port of the injection device into the reservoir for cleaning the reservoir (Step S113).

In conclusion, the present invention proposes an injection device, a semiconductor testing system and a semiconductor testing method, wherein the injection device has a built-in cleaning mechanism, which can flexibly set different cycles of injecting liquid, testing semiconductor elements and cleaning semiconductor elements, whereby is upgraded the efficiency and precision of testing semiconductor elements, and whereby is effectively reduced the risk that testing liquids pollute semiconductor elements. Besides, the cleaning mechanism can be programmed to undertake cleaning while the machine is used for the first time.

The embodiments have been described above to demonstrate the technical thoughts and characteristics of the present invention to make the persons skilled in the art to understand, make, and use the present invention. However, these embodiments are not intended to limit the scope of the present invention. Any equivalent modification or variation according to the spirit of the present invention is to be also included by the scope of the present invention.

What is claimed is:

1. A semiconductor testing method comprising steps:
   placing a semiconductor element on a supporter, wherein the semiconductor element has a plurality of electrode pads and a test area;
   providing a testing member including a plurality of electric-conduction elements and at least one opening, wherein the position of the opening is corresponding to the test area, and wherein the plurality of electric-conduction elements contacts the plurality of electrode pads of the semiconductor element;
   providing an injection device including a reservoir, wherein the reservoir has at least one connecting port and a dropping port;
   actuating the dropping port of the injection device to pass through the opening of the testing member and contact the test area of the semiconductor element;
   injecting a first testing liquid through the at least one connecting port of the injection device into the reservoir, and letting the first testing liquid contact the test area of the semiconductor element through the dropping port for testing electric signals of the semiconductor element;
   injecting a cleaning liquid through the at least one connecting port of the injection device into the reservoir for cleaning the reservoir and the test area of the semiconductor element;
   actuating the dropping port of the injection device to depart from the test area of the semiconductor element;
   before the dropping port of the injection device is contacting the test area of the semiconductor element, driving a blocking element of the injection device to press against the dropping port of the injection device; and
   injecting the cleaning liquid through the at least one connecting port of the injection device into the reservoir for cleaning the reservoir.

2. The semiconductor testing method according to claim 1 further comprising a step:
   before separating the dropping port of the injection device from the test area of the semiconductor element, injecting a second testing liquid through the at the least one connecting port of the injection device into the reservoir to let the second testing liquid contact the test area of the semiconductor element for testing electric signals of the semiconductor element.

3. The semiconductor testing method according to claim 1 further comprising steps:
   before separating the dropping port of the injection device from the test area of the semiconductor element, injecting a second testing liquid through the at the least one connecting port of the injection device into the reservoir to let the second testing liquid contact the test area of the semiconductor element for testing electric signals of the semiconductor element; and
   injecting the cleaning liquid through the at the least one connecting port of the injection device into the reservoir for cleaning the reservoir and the test area of the semiconductor element.

4. The semiconductor testing method according to claim 1 further comprising a step:
   draining off the first testing liquid before injecting the cleaning liquid.

5. The semiconductor testing method according to claim 1 further comprising a step:
   draining off the cleaning liquid before separating the dropping port of the injection device from the test area of the semiconductor element.

* * * * *